(12) United States Patent
Bunschoten et al.

(10) Patent No.: US 7,871,995 B2
(45) Date of Patent: *Jan. 18, 2011

(54) DRUG DELIVERY SYSTEM COMPRISING A TETRAHYDROXYLATED ESTROGEN FOR USE IN HORMONAL CONTRACEPTION

(75) Inventors: Evert Johannes Bunschoten, Heesch (NL); Herman Jan Tijmen Coelingh Bennink, Driebergen (NL); Christian Franz Holinka, New York, NY (US)

(73) Assignee: Pantarhei Bioscience B.V., Al Zeist (NL)

( * ) Notice: Subject to any disclaimer, the term of this patent is extended or adjusted under 35 U.S.C. 154(b) by 1233 days.

This patent is subject to a terminal disclaimer.

(21) Appl. No.: 10/478,357

(22) PCT Filed: May 23, 2002

(86) PCT No.: PCT/NL02/00330

§ 371 (c)(1),
(2), (4) Date: May 25, 2004

(87) PCT Pub. No.: WO02/094278

PCT Pub. Date: Nov. 28, 2002

(65) Prior Publication Data

US 2004/0192620 A1    Sep. 30, 2004

(30) Foreign Application Priority Data

May 23, 2001 (EP) ................. 01201945
May 23, 2001 (EP) ................. 01201946
May 23, 2001 (EP) ................. 01201947
Aug. 31, 2001 (EP) ................. 01203305
Nov. 15, 2001 (EP) ................. 01204377

(51) Int. Cl.
*A61K 31/56* (2006.01)

(52) U.S. Cl. ................... 514/171; 514/182
(58) Field of Classification Search ............ 514/171, 514/182

See application file for complete search history.

(56) References Cited

U.S. PATENT DOCUMENTS

| | | | |
|---|---|---|---|
| 3,440,320 A | 4/1969 | Sackler et al. | |
| 3,797,494 A | 3/1974 | Zaffaroni | |
| 4,460,372 A | 7/1984 | Campbell et al. | |
| 4,573,996 A | 3/1986 | Kwiatek et al. | |
| 4,624,665 A | 11/1986 | Nuwayser | |
| 4,722,941 A | 2/1988 | Eckert et al. | |
| 4,762,717 A | 8/1988 | Crowley, Jr. | |
| 4,937,238 A | 6/1990 | Lemon | |
| 5,063,507 A | 11/1991 | Lindsey et al. | |
| 5,130,137 A | 7/1992 | Crowley, Jr. | |
| 5,211,952 A | 5/1993 | Spicer et al. | |
| 5,223,261 A | 6/1993 | Nelson et al. | |
| 5,340,584 A | 8/1994 | Spicer et al. | |
| 5,340,585 A | 8/1994 | Pike et al. | |
| 5,340,586 A | 8/1994 | Pike et al. | |
| 5,468,736 A | 11/1995 | Hodgen | |
| 5,633,242 A | 5/1997 | Oettel et al. | |
| 5,662,927 A | 9/1997 | Ehrlich et al. | |
| 5,827,843 A | 10/1998 | Koninckx | |
| 6,214,815 B1 | 4/2001 | Shangold et al. | |
| 6,500,814 B1 | 12/2002 | Hesch | |
| 2002/0183299 A1 | 12/2002 | Voskuhl | |

FOREIGN PATENT DOCUMENTS

| | | | |
|---|---|---|---|
| DE | 2336433 A1 | 4/1975 | |
| DE | 2336434 A1 | 4/1975 | |
| DE | 2426779 A1 | 12/1975 | |
| DE | 19917930 A1 | 10/2000 | |
| EP | 0402950 A | 12/1975 | |
| EP | 468690 A1 | 1/1992 | |
| EP | 1700602 A1 | 5/2001 | |
| WO | 9218107 A1 | 10/1992 | |
| WO | 9426207 | 11/1994 | |
| WO | 9502408 A1 | 1/1995 | |
| WO | 9517895 | 7/1995 | |
| WO | 9603929 A1 | 2/1996 | |
| WO | 9858657 A1 | 12/1998 | |
| WO | 0062753 | 10/2000 | |
| WO | 0073416 A1 | 12/2000 | |

| | | |
|---|---|---|
| WO | 0130357 A1 | 5/2001 |
| WO | 0185154 A2 | 11/2001 |

OTHER PUBLICATIONS

Katzung, Basic and Clinical Pharmacology, 6th ed., 1995, pp. 608-624.*
Tseng et al., "Heterogeneity of Saturable Estradiol Binding Sites in Nuclei of Human Endometrium. Estetrol Studies", (1978), vol. 9, pp. 1145-1148.
Fishman et al., "Fate of 15 α-Hydroxyestriol-3H in Adult Man", J. Clin. Endocrinol. Metab., (1970), vol. 31, pp. 436-438.
Levine et al., "Uterine vascular effects of estetrol in nonpregnant ewes", Am. J. Obstet. Gynecol., (1984), [148], vol. 73, pp. 735-738.
Martucci et al., "Direction of Estradiol Metabolish as a Control of its Hormonal Action—Uterotrophic Activity of Estradiol Metabolites", Endocrin., (1977), vol. 101, pp. 1709-1715.
Martucci et al., "Uterine Estrogen Receptor Binding of Catecholestrogens and of Estetrol (1,3,5(10)-Estratriene-3, 15a, 16a, 17 β-Tetrol)", Steroids, (1976), vol. 27, pp. 325-333.
Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.
Tseng et al., "Competition of Estetrol and Ethynylestradiol with Estradiol for Nuclear Binding in Human Endometrium", Journal of Steroid Biochemistry, (1976), vol. 7, pp. 817-822.
Visser et al., "In vitro effects of estetrol on receptor binding, drug targets and human liver cell metabolism," Climacteric (2008) 11(1) Appx. II: 1-5.
Visser et al., "First human exposure to exogenous single-dose oral estetrol in early postmenopausal women," Climacteric (2008) 11(1): 1-10.
Visser et al., "Clinical applications of estetrol," J. Of Steroid Biochem and Molecular Biol. (2009) 114: 85-89.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," Climacteric (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Allen et al., An Ovarian Hormone: Preliminary Report on Its Localization, Extraction and Partial Purification, and Action in Test Animals, JAMA, Sep. 8, 1923, vol. 81, pp. 819-821.
Allen et al., The Induction of a Sexually Mature Condition in Immature Females by Injection of the Ovarian Follicular Hormone, Am. J. Physiol., 1924, vol. 69, pp. 577-588.
Jones et al., The Effects of Various Steroids on the Vaginal Histology in the Rat, Fertility and Sterility, Apr. 1973, vol. 24, No. 4, pp. 284-291.
Tulchinsky et al., Plasma Esterol as an Index of Fetal Well-Being, J. Clin. Endocrinol. Metab., 1975, vol. 40. pp. 560-567.
Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.
Hammond et al., A Versatile Method for the Determination of Serum Cortisol Binding Globulin and Sex Hormone Binding Globulin Binding Capacities, 1983, vol. 132, pp. 101-110.
Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.
Murphy et al., Endometrial Effects of Long-Term Low-Dose Administration of RU486, Fertility and Sterility, Apr. 1995, vol. 63, No. 4, pp. 761-766.
Reel et al., Survey and Assessment of Mammalian Estrogen Biological Assays for Hazard Characterization, Fundamental and Applied Toxicology, 1996, vol. 34, pp. 288-305.

Beral et al., Use of HRT and the Subsequent Risk of Cancer, Journal of Epidemiology and Biostatistics, 1999, vol. 4, No. 3, pp. 191-215.
Tavani et al., The Adverse Effects of Hormone Replacement Therapy, Drugs & Aging, May 1999, vol. 14, No. 5, pp. 347-357.
Pike et al., Progestins and Menopause: Epidemiological Studies of Risks of Endometrial and Breast Cancer, Steroids, 2000, vol. 65, pp. 359-664.
Avvakumov et al., Steroid-binding Specificity of Human Sex Hormon-binding Globulin Is Influenced by Occupancy of a Zinc-binding Site, The Journal of Biological Chemistry, Aug. 25, 2000, vol. 275, No. 34, pp. 25920-25925.
Holinka et al., "In Vivo Effects of Esterol on the Immature Rat Uterus", Biology of Reproduction, Society for the Reproduction Society for the Study of Reproduction, Champaign, IL, US, Mar. 1979, vol. 20, No. 2, pp. 242-246.
Holinka, et al., "Comparison of Effects of Esterol and Tamoxifen with Those of Estriol and Estradiol on the Immature Rat Uterus", Biology of Reproduction, Society for the Reproduction Society for the Study of Reproduction, Champaign, IL, US, 1980, vol. 22, No. 4, pp. 913-926.
Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.
Erdbruegger et al., Drug Discovery Today: Disease Mechanisms (2004), vol. 1, pp. 73-81.
Lab Tests Online (www.labtestsonline.org/understanding/conditions/autoimmune.html) retrieved on Oct. 15, 2009.
www.tiscali.co.uk/lifestyle/healthfitness/health_advice/netdoctor/archive/000489.html, retrieved on Oct. 15, 2009.
MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.
MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also see WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.
Mueck et al., "Angio and Anti-Angiogenetic Effects of Estradiol and its Metabolites", J. Clin. Basic Cardiol., 2001, pp. 153-155, vol. 4, No. 2.
Shah et al., "Estrogen and Skin. An Overview", Am. J. Clin. Dermatol., 2001, pp. 143-150, vol. 2, No. 3.
Sitruk-Ware et al., "Local Hormonal Treatment for Urogenital Atrophy After Menopause", Shweiz. Rundsch, Med. Praxis, 1997, pp. 1245-1248, vol. 86, No. 33, and Sitruk-Ware, English Translation, 1997. Praxis, Schweizerische Rundschau fur Medizin, vol. 86, No. 33, pp. 1-13.
Schmidt et al., "Treatment of Skin Aging with Topical Estrogens", Int. J. Dermatol., 1996, pp. 669-674, vol. 35, No. 9.
Younglai et al., Journal of Clinical Endocrinology and Metabolism, 1968, vol. 28, Issue 11, pp. 1611-1617.
Webster Ninth New Collegiate Dictionary, 2000, Definition of Prevention, p. 1.
Willhite et al., Pharmacotherapy, 2001, vol. 21, Issue 4, pp. 464-480.
Kuipers et al., "Enterohepatic Circulation in the Rat", Gastroenterol., vol. 88, pp. 403-411 (1985).
Schwartz, "A Model for the Regulation of Ovulation in the Rat", Recent Prog. Horm. Res., vol. 25, pp. 1-55, (1969).
Beattie et al., "The Differential Effects of Diestrous Progestogen Administration on Proestrous Gonadotrophin Levels, Endocrinol", vol. 97, pp. 885-890, (1975).
De Visser et al., Endocrinological Studies with (7a, 17 a)-Hydroxy-7-me norpregn-5(10)-en-20-yn-3-one (Org OD 14), Arzneim, Forsh., vol. 34, pp. 1010-1020, (1984).
National Cancer Institute: Breast cancer prevention retrieved online Aug. 7, 2007 from the internet; http://www.cancer.gov/templates/doc.aspx?viewed+D972A74B-D25A-4F86-B8ED-33EB3C0450E4&version, p. 1.

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.
National Institute of Child Health and Human Development, NIH Publication No. 02-2413 retrieved online on Aug. 9, 2007.
Breast Cancer Prevention retrieved online Aug. 7, 2007 from the internet; http://www.cancer.gov/cancertopics/pdq/prevention/breast/Patient/page 3.
Prophylactic definition—Medical Dictionary of Popular Medical Terms; retrieved on Mar. 14, 2008 via www.medterms.com/script/main/art.asp?articlekey+11902.
Zips et al., in vivo, 2005, vol. 19, pp. 1-8.
Holinka et al., Biology of Reproduction, 1980, vol. 22, pp. 913-926.
Martucci et al., "Impact of Continuously Administered Catechol Estrogens on Uterine Growth and Luteinizing Hormone Secretion", Endocrinology (Dec. 1979), vol. 105, No. 6, pp. 1288-1292.
Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.
Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.
Shanklin et al., "Aqueous Estrogens in the Management of Respiratory Distress SYndrome", J. Reprod. Med. (Aug. 1970), vol. 5, No. 2, pp. 53-71.
Chemical Abstracts Service, Columbus Ohio, US: Jakowicki, "Evaluation of Estriol Level In the Amniotic Fluid in Prolonged Pregnancy", XP002458625, 1979.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.
Fogary, Jr., "Postmaturity", J. Am. Osteopath. Assoc., (Jan. 1976), vol. 75, No. 5, pp. 512-517.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.

* cited by examiner

*Primary Examiner*—San-ming Hui
(74) *Attorney, Agent, or Firm*—The Webb Law Firm

(57) ABSTRACT

A method of contraception in mammalian females, which method comprises the parenteral or rectal administration of an estrogenic component and a progestogenic component to a female of childbearing capability in an amount effective to inhibit ovulation, wherein the estrogenic component is selected from the group consisting of substances represented by the following formula (1)

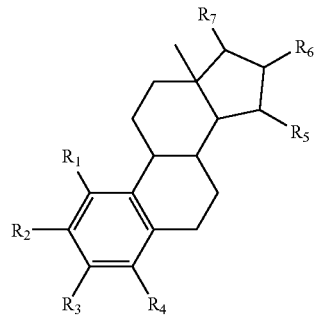

in which $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors. Another aspect of the invention concerns a drug delivery system for parenteral or rectal administration that contains the aforementioned estrogenic component and a progestogenic component, said drug delivery system being selected from the group consisting of suppositories, systems for intravaginal delivery, inhalers, nasal sprays and transdermal delivery systems.

2 Claims, 1 Drawing Sheet

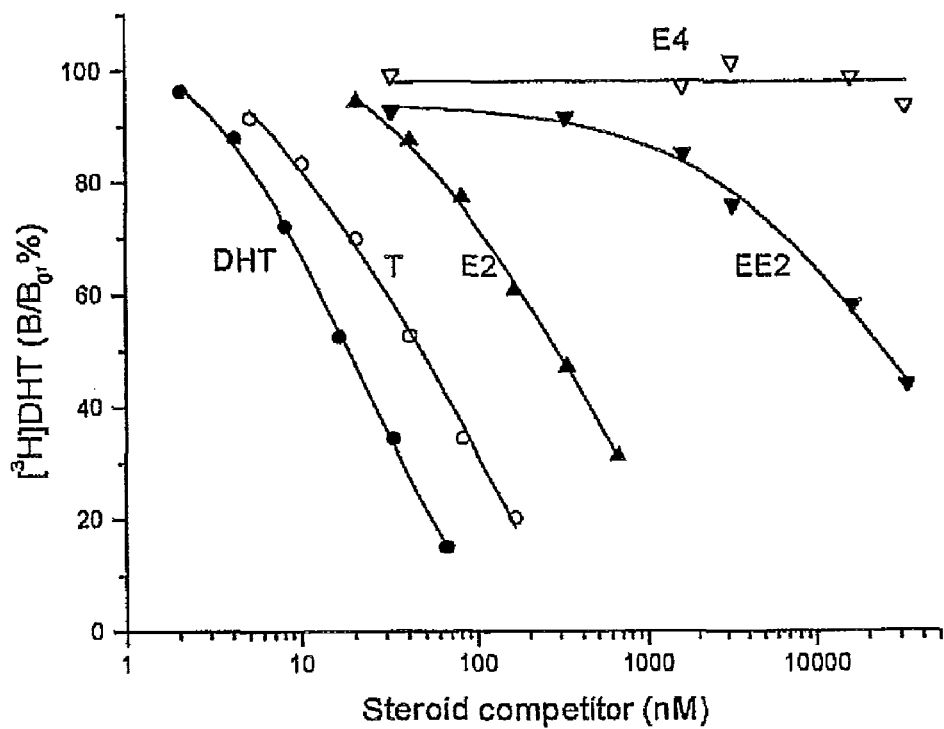
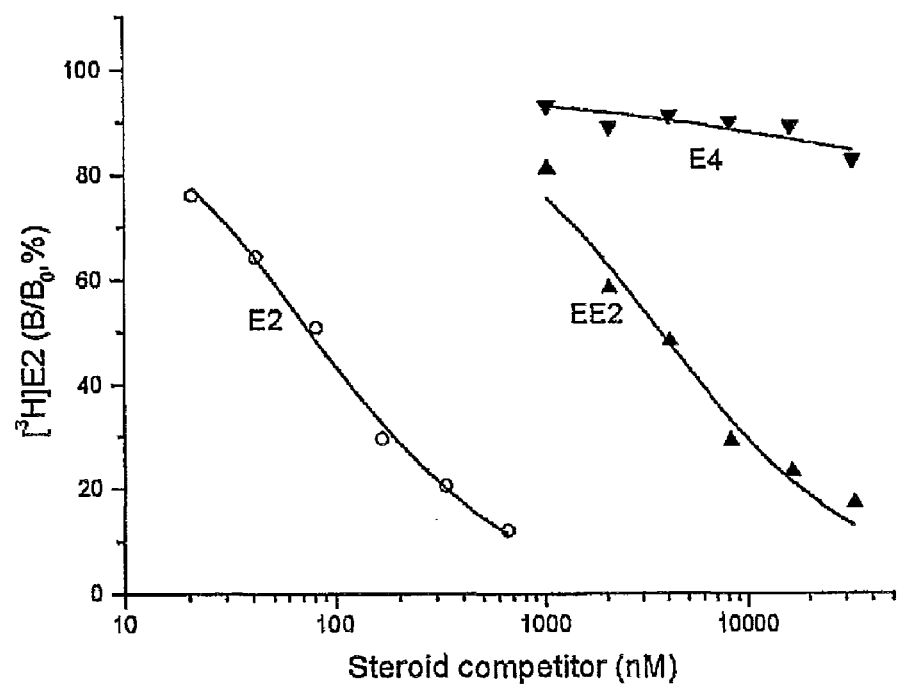

DRUG DELIVERY SYSTEM COMPRISING A TETRAHYDROXYLATED ESTROGEN FOR USE IN HORMONAL CONTRACEPTION

TECHNICAL FIELD OF THE INVENTION

The present invention relates to a method of hormonal contraception in mammalian females. More particularly the invention is concerned with a method of hormonal contraception that comprises the parenteral or rectal administration of a combination of an estrogenic component and a progestogenic component to a female of childbearing capability in an effective amount to inhibit ovulation.

The invention also encompasses a pharmaceutical kit comprising the aforementioned estrogenic component and a progestogenic component.

BACKGROUND OF THE INVENTION

Estrogens play an important major role in existing methods of hormonal contraception. For contraception estrogens are commonly used together with a progestogen, e.g. levonorgestrel, desogestrel, norethisterone, cyproterone acetate, dienogest. The estrogens are needed for inhibiting follicle maturation and ovulation, but in addition they replace the endogenous ovarian secretion of estradiol which is suppressed to a major extent by the administration of a hormonal contraceptive. This replacement is important for preventing estrogen deficiency and for maintaining an artificial menstrual cycle and other genital functions.

Endogenous and exogenous estrogens fulfil important central nervous and metabolic functions in the female organism: normal estrogen levels make a decisive contribution to a woman's well-being. Notwithstanding the widespread use of estrogens in hormonal contraceptives, there are still some unsolved problems. Known estrogens, in particular the biogenic estrogens (i.e. estrogens that occur naturally in the human body), are eliminated from the blood stream very quickly. For instance, for the main human biogenic estrogen 17β-estradiol the half-life is around 1 hour. As a result, between separate administration events, blood serum levels of such biogenic estrogens tend to fluctuate considerably. Thus, shortly after administration the serum concentration is usually several times higher than the optimum concentration. In addition, if the next administration event is delayed, serum concentrations will quickly decrease to a level where the estrogen is no longer physiologically active. This is particularly undesirable in contraceptive methods.

The most important synthetically altered estrogenic steroid is 17α-ethinyl estradiol (EE). This estrogen is dominant in oral hormonal contraception. Apart from EE, mestranol has been used in a few cases; mestranol is a "prodrug" that is metabolised to EE in the organism. The liver is a target organ for estrogens. The secretion activity that is affected by estrogens in the human liver includes increased synthesis of transport proteins CBG, SHBG, TBG, several factors that are important for the physiology of blood clotting, and lipoproteins. The strong hepatic estrogenicity of ethinyl estradiol and diethylstilbestrol (DES), especially their effects on haemostasis factors, may explain why these synthetic estrogens have been associated with the enhanced risk of thromboembolism. Other undesirable side-effects that have been reported in relation to the use of synthetic estrogens include fluid retention, nausea, bloating, cholelithiasis, headache and breast pain.

The aforementioned deficits are of considerable clinical significance when commonly known biogenic or synthetic estrogens are applied. Consequently, there is an as yet unmet need for estrogens that do not display these deficits and which can suitably be employed in contraceptive methods for females because of their ability to (a) reliably suppress follicle maturation and ovulation and to (b) effectively replace the endogenous ovarian secretion of 17β-estradiol.

SUMMARY OF THE INVENTION

The inventors have surprisingly found that these objectives are met by estrogenic substances that are represented by the following formula

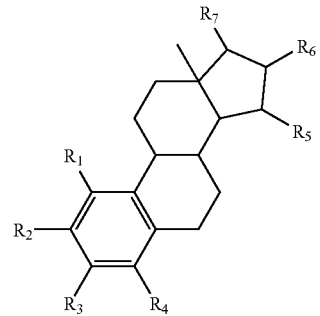

in which formula $R_1$, $R_2$, $R_3$, $R_4$ independently are a hydrogen atom, a hydroxyl group or an alkoxy group with 1-5 carbon atoms; each of $R_5$, $R_6$, R7 is a hydroxyl group; and no more than 3 of $R_1$, $R_2$, $R_3$, $R_4$ are hydrogen atoms.

A known representative of this group of estrogenic substances is 1,3,5 (10)-estratrien-3, 15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et. al., 1975. J. Clin. Endocrinol. Metab., 40, 560-567).

In 1970,Fishman et al., "Fate of 15α-hydroxyestriol-$^3$H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

- Levine et al., 1984. Uterine vascular effects of estetrol in nonpregnant ewes. Am. J. Obstet. Gynecol., 148:73, 735-738: "When intravenously administered in nonpregnant ewes, estetrol is 15 to 30 times less potent than estriol and 17β-estradiol in uterine vasodilation".
- Jozan et al., 1981. Different effects of oestradiol, oestriol, oestetrol and of oestrone on human breast cancer cells (MCF-7) in long term-tissue culture. Acta Endocrinologica, 98, 73-80: "Estetrol agonistic potency is 2% of the magnitude observed for 17β-estradiol in in vitro cell proliferation".
- Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha, 17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be lower than that of another biogenic estrogen, namely, 17β-estradiol, which is considered to be a relatively weak estrogen (e.g. compared to ethinyl estradiol). With these findings in mind, it is not surprising that the interest in estetrol has dwindled since the early eighties and that no publications on the properties of estetrol have been issued since.

U.S. Pat. No. 5,468,736 (Hodgen) describes a method of hormone replacement therapy involving the administration of estrogen together with an amount of antiprogestin (antiprogestogen), which inhibits estrogen-induced endometrial proliferation in women. In Example 3 the combined use of estetrol and lilopristone is mentioned. No clues are given in the examples as to the mode and frequency of administration or regarding the dosage level employed. A disadvantage associated with the use of antiprogestogens, such as lilopristone, is the risk of inducing abnormal endometrial morphology, i.e. cystic hyperplasia, as has been observed in women who received an antiprogestogen treatment against endometriosis (Murphy et al., 1995. Fertil. Steril., 95, 761-766).

U.S. Pat. No. 5,340,586 (Pike et al.) is concerned with compositions and methods which are effective to treat oophorectomised women, wherein an effective amount of an estrogenic composition and an androgenic composition are provided over a period of time. In the US-patent it is stated that natural and synthetic estrogenic compositions that can be used include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate, and furthermore that equine estrogens, such as equilelinin, equilelinin sulfate and estetrol, may also be employed. Except for the exhaustive inventory of known estrogens, no other reference to estetrol (which is erroneously referred to as an equine estrogen) is made in this US-patent.

The same exhaustive list of estrogens is found in the following patent documents:

U.S. Pat. No. 4,762,717 (Crowley): A contraceptive method comprising the sequential administration of (1) a combination of luteinizing hormone releasing hormone (LHRH) and estrogen and (2) a combination of LHRH and estrogen and progestogen.

U.S. Pat. No. 5,130,137 (Crowley): A method of treating benign ovarian secretory disorder comprising the sequential administration of (1) a combination of luteinizing hormone releasing hormone (LHRH) and estrogen and (2) a combination of LHRH and estrogen and progestogen.

U.S. Pat. No. 5,211,952 (Spicer et al.): A contraceptive method comprising administering a gonadotropin hormone releasing hormone (GnRH) composition in an amount effective to inhibit ovulation and administering estrogen and progestogen to maintain serum levels above a defined minimum level.

U.S. Pat. No. 5,340,584 (Spicer et al.): A method for preventing conception or for treating benign gynaecological disorders comprising administering a GnRH composition for a first period of time in an amount effective to suppress ovarian estrogen and progesterone production, simultaneously administering an estrogenic composition in an amount effective to prevent symptoms of estrogen deficiency and simultaneously administering a progestogen in an amount effective to maintain serum level of said progestogen at a level effective to decrease endometrial cell proliferation.

U.S. Pat. No. 5,340,585 (Pike et al.): A method of treating benign gynaecological disorders in a patient in whom the risk of endometrial stimulation by estrogenic compositions is minimised or absent, comprising administering a GnRH composition in an amount effective to suppress ovarian estrogen and progesterone production and administering an estrogenic composition in an amount effective to prevent symptoms of estrogen deficiency.

WO 00/73416 (Yifang et al.): A method for regulating the fertility of a host, comprising contacting host ovarian cells with a safe and effective amount of a pharmaceutical composition comprising an antisense oligonucleotide that is complementary to the nucleotide sequence of the follicle stimulating hormone (FSH) receptor. The possibility of combined administration of such an antisense oligonucleotide with an estrogenic steroid is mentioned in the application.

The benefits of the present invention may be realised without the co-administration of anti-progestogens, LHRH compositions, GnRH compositions and/or antisense oligonucleotides that are complementary to the nucleotide sequence of the follicle stimulating hormone (FSH) receptor as proposed in the aforementioned publications. Also, the present invention may suitably be applied in individuals who have not been oophorectomised, or in whom the risk of endometrial stimulation by estrogenic compositions is not minimised or absent, other than by combined administration of a progestogen and an estrogen, e.g. as a result of hysterectomy. Furthermore the present method does not require the use of a slow release formulation as is dictated by most of the aforementioned US-patents.

In view of the low estrogenic potency of the estetrol-like substances that are employed in accordance with the invention, it is surprising that these substances can effectively be used in a contraceptive method. Although the inventors do not wish to be bound by theory, it is believed that the unexpected efficacy of parenterally or rectally administered estetrol-like substances results from the combination of unforeseen favourable pharmacokinetic (ADME) and pharmacodynamic properties of these substances.

As regards the pharmacokinetic properties of the present estrogenic substances the inventors have discovered that their in vivo half-life is considerably longer than that of other biogenic estrogens. Thus, even though estetrol and estetrol-like substances have relatively low estrogenic potency, they may effectively be employed in a contraceptive method because their low potency is compensated for by a relatively high metabolic stability, as demonstrated by a long half-life.

An advantageous property of the present estrogenic substances resides in the fact that sex hormnone-binding globulin (SHBG) hardly binds these estrogenic substances, meaning that, in contrast to most known estrogens, serum levels are representative for bio-activity and independent of SHBG levels.

Another important benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenytoin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention hardly suffer from drug-drug iiiteractions.and thus produce a very consistent, i.e. predictable, impact. Thus, the efficacy of the estrogenic substances of the invention is highly reliable, which is particularly important in the field of contraception.

BRIEF DESCRIPTION OF THE DRAWINGS

FIG. 1 contains two line-charts showing the competitive displacement of [$_3$]DT (panel A) and [3H]estradiol (panel B) from the human sex hormone-binding globulin steroid binding site. The unlabeled steroid ligands used as competitors were as follows: estetrol (E4), 17α-ethinyl estradiol (EE2), 17β-estradiol (E2), testosterone (T) and 5α-hihydrotestosterone (DHT).

DETAILED DESCRIPTION OF THE INVENTION

Accordingly one aspect of the present invention relates to a method of contraception in mammalian females, which method comprises the parenteral or rectal administration of an estrogenic component and a progestogenic component to a female of childbearing capability in an amount effective to inhibit ovulation, wherein the estrogenic component is selected from the group consisting of:

substances represented by the following formula

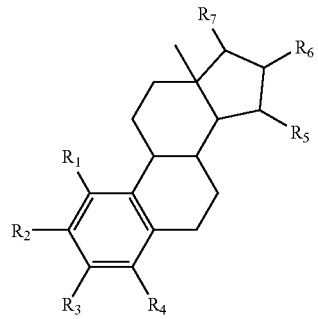

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;

precursors capable of liberating a substance according to the aforementioned formula when used in the present method; and mixtures of one or more of the aforementioned substances and/or precursors. The term "parenteral administration" as used in here encompasses transdermal, intranasal, intravaginal, pulmonary, buccal, subcutaneous, intramuscular and intrauterine administration.

The term "estrogenic component" as used throughout this document encompasses substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body. The term "progestogenic component" is defined as a substance that is capable of triggering an progestogenic response in vivo or a precursor which is capable. of liberating such a substance in vivo. Usually progestogenic components are capable of binding to a progestogen receptor.

It is noted that the present invention not only encompasses the use of estrogenic and progestogenic components specifically mentioned in this application, but also metabolites of these hormones that display comparable in vivo functionality. In this context it is observed that, for instance, levonorgestrel is a metabolite of norgestimate and that estriol is a metabolite of 17beta-estradiol. Both these progestogens and estrogens have found application in contraceptive formulations and/or hormone replacement therapy. The term "estrogenic substances" as used in this document does not encompass tritium ($^3$H) labeled estrogenic substances such as tritium labeled estetrol.

The present estrogenic substances are distinct from both the biogenic and synthetic estrogens that are commonly applied in pharmaceutical formulations in that they contain at least 4 hydroxyl groups. The present substances are special in that the 5 membered ring in the steroid skeleton comprises 3 hydroxyl substituents rather than 0-2.

Known estrogens that contain at least 4-hydroxyl groups and derivatives thereof are:
1,3,5(10)-estratrien-2,3,15α,16α,17β-pentol 2-methyl ether
1,3,5(10)-estratrien-2,3,15β,16α,17β-pentol 2-methyl ether
1,3,5(10)-estratrien-2,3,16α,17β-tetrol
1,3,5(10)-estratrien-3,4,16α,17β-tetrol 4-methyl ether
1,3,5(10)-estratrien-3,15α,16α,17β-tetrol
1,3,5(10)-estratrien-3,15α,16α,17β-tetrol tetra acetate
1,3,5(10)-estratrien-3,15β,16β,17β-tetrol tetra acetate Preferably, the estrogenic substance applied as the active component in the present composition is a natural estrogen, i.e. an estrogen that is found in nature and especially in mammals. Even more preferably, the estrogenic substance is a so called biogenic estrogen, i.e. an estrogen that occurs naturally in the human body, a precursor of a biogenic estrogen or mixtures thereof. Because biogenic estrogens are naturally present in the fetal and female body, side-effects are not expected to occur, particularly not if the serum levels resulting from the exogenous administration of such estrogens do not substantially exceed naturally occurring concentrations. Since estetrol serum levels in the fetus are several times higher than those found in pregnant females and knowing that the fetus is particularly vulnerable, estetrol is deemed to be a particularly safe biogenic estrogen. Side-effects are not expected to occur, particularly not if the serum levels resulting from the exogenous administration of such estrogens do not substantially exceed naturally occurring (fetal) concentrations. With synthetic estrogens such as ethinyl estradiol there is a (dose dependent) risk of undesirable side-effects, such as thromboembolism, fluid retention, nausea, bloating, cholelithiasis, headache and breast pain.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another. preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5 (10)-estratrien-3,15, 16,17-tetrol. A preferred isomer of the latter substance is 1,3,5 (10)-estratrien-3,15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through iiz vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosidic residue containing 1-20 glycosidic units per residue.

Typical examples of precursors which can suitably be used in accordance with the invention are esters that can be obtained by reacting the hydroxyl groups of the estrogenic substances with substances that contain one or more carboxy ($M^{+-}OOC$—) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms., The present method usually employs uninterrupted parenteral or rectal administration of the estrogenic component during a period of at least 10 days, preferably of at least 20 days.

The term "uninterrupted" as used in here, means that the estrogenic component is administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be continuous if the longest interval between 2 subsequent administrations is not more than 3.5 times as long as the average interval. Even more preferably said longest interval is not more than 2.5 times, most preferably not more than 1.5 times as long as the average interval.

In the present method, the estrogenic and progestogenic component may be administered in separate dosage units. However, it is also possible and indeed very convenient to combine these two components into a single dosage unit.

In the contraceptive method according to the present invention the combination of the progestogenic and estrogenic component is suitably administered uninterruptedly during a period of at least 10 days so as to achieve effective ovulation inhibition for a period of at least 20 days.

The invention may suitably be reduced to practice in the form of a variety of contraceptive methods that are known to the person skilled in the art. Amongst these methods are the so called "combined" methods. The combined methods make use of monophasic preparations, which contain dosage units with a constant amount of an estrogen and a progestogen or bi- or triphasic preparations which have varying levels of estrogen and progestogen; in most cases consisting of relatively constant levels of estrogen with a step-wise increase in progestogen throughout the cycle. The combined methods have in common that they are based on a regimen which involves an administration-free interval of about 7 days whereby withdrawal bleeding, simulating the natural menses, occurs. Thus 21 day intervals of hormone administration alternate with 7 days during which no hormones are administered.

As an alternative to the aforementioned combined methods, the so called "sequential" method has been proposed. Typical of the sequential method is that it comprises two consecutive phases, i.e. one phase during which estrogen and no progestogen is administered and another phase during which a combination of estrogen and progestogen is administered. The first contraceptive sequential methods, like the aforementioned combined methods, made use of an administration free interval of about 7 days. More recently, sequential methods have been proposed which do not include an administration-free (or placebo) period, meaning that estrogen is administered throughout the full cycle and that progestogen is co-administered during only part of that cycle. WO 95/17895 (Ehrlich et al.) describes such an uninterrupted sequential method.

Yet another example of a contraceptive method which is encompassed by the present invention is the so called "continuous combined" method, which is a particular version of the combined method that uses uninterrupted combined administration of a progestogenic and an estrogenic component during a prolonged period of time, e.g. more than 50 days. In contrast to ordinary combined and sequential methods, no regular menses occur in the continuous combined method as the continuous administration of progestogen in the indicated amounts induces amenorrhoea.

In one embodiment of the invention, which relates to the continuous combined method, the present method comprises the uninterrupted parenteral or rectal administration of the combination of the estrogenic component and the progestogenic component during a period of at least 28,preferably at least 60 days.

In another embodiment of the invention,. which relates to sequential and combined methods that employ a significant administration-free interval, the method of the invention comprises an interval of at least 2 days, preferably from 3-9 days, most preferably from 5-8 days, during which no progestogenic component and no estrogenic component is administered and wherein the resulting decrease in serum concentration of the progestogenic component and the estrogenic component induces menses.

Yet another embodiment of the invention, which concerns a sequential method without a significant pause, is characterised in that it comprises the uninterrupted parenteral or rectal administration of the estrogenic component during a period of at least 28 days, preferably at least 60 days, and in that, following the combined administration of the estrogenic component and the progestogenic component, the estrogenic component and no progestogenic component are administered during 3-18 consecutive days, preferably during 5-16 consecutive days and the resulting decrease in serum concentration of the progestogenic component should normally be sufficient to induce menses.

The mode of administration employed in the present method is suitably selected from the group consisting of transdermal, intranasal, intravaginal, rectal, pulmonary, buccal, subcutaneous, intramuscular or intrauterine administration. In a particularly preferred embodiment the present method employs transdermal, intravaginal, intranasal or rectal administration. Even more preferably the present method employs transdermal or intranasal administration. The most preferred mode of administration is transdermal administration.

Rectal, intranasal, buccal and pulmonary administration are ideally suited for (at least) once daily administration. Transdermal administration is advantageously applied at frequencies between once a day and once a month. Intravaginal and intrauterine administrations are advantageously operated at administration frequencies between once weekly and once monthly. Subcutaneous and intramuscular administration are suitably done in the form of depot injections at intervals of 1 week to 6 months, preferably at intervals of 4 weeks to 3 months.

For reasons of convenience and also to achieve high compliance rates, the present method preferably utilises administration intervals of 1 day, 1 week or 1 month. Regimens that employ once daily intranasal administration, once weekly transdermal administration or once monthly intravaginal or subcutaneous administration are particularly preferred.

Irrespective of the mode of administration, the estrogenic component is preferably administered in an amount effective to achieve a blood serum concentration of at least 1 nanogram per litre, more preferably of at least 10 nanogram per litre, most preferably at least 100 nanogram per litre. Generally the resulting blood serum concentration of the estrogenic component will not exceed 100 μg per litre, preferably it will not exceed 50 μg per litre, more preferably it will not exceed 25 μg per litre.

In accordance with the present method the estrogenic component is usually administered in an amount of less than 1 mg per kg of bodyweight per day, preferably of less than 0.4 mg per kg of bodyweight per day, more preferably of less than 0.2 mg per kg of bodyweight per day. In order. to achieve a significant impact from the administration of the estrogenic component, it is advisable to administer in an amount of at least 1 μg per kg of bodyweight per day. Preferably, the administered amount is at least 2 μg per kg of bodyweight per day, more preferably at least 5 μg per kg of bodyweight per day. The aforementioned dosages are to be construed as averaged daily dosages in case administration intervals of more than 1 day are used.

In the present method, particularly when used in humans, the estrogenic component is usually administered parenterally or rectally in an average dosage of at least 0.05 mg per day, preferably of at least 0.1 mg pet day. The maximum parenteral or rectal dosage is normally kept below 40 mg per day, preferably below 20 mg per day.

In all of the aforementioned methods it is preferred to parenterally or rectally administer the estrogenic component and the progestogenic component during a period of at least 10,preferably of at least 20 days. In case of a sequential method without pause or a continuous combined method it is preferred to administer the estrogenic component and/or the progestogenic component uninterruptedly during a period of at least 30 days, more preferably of at least 60 days, most preferably of at least 150 days. Uninterrupted sequential contraceptive methods, which employ continuous estrogen administration, exhibit an optimum combination of contraceptive reliability and cycle control. The combination of a pause of 6-7 days during which significant follicular development occurs and the well documented bad compliance of many pill-users (30%-40% forget pills occasionally) cause an increased risk of escape ovulation especially if the pause is (unintentionally) extended. This results in "real life" pregnancy rates of 3-8% per year. By removing the pause and administering ovulation inhibiting steroids at least once daily, the risk of escape ovulation is much lower.

The general concerns about the so called unopposed administration of estrogen, i.e. administration of estrogen without co-administered progestogen might cause hyperplasia of the endometrium, are less applicable to the estrogenic components of the present invention. Therefore, in a particularly preferred embodiment, the present contraceptive method is executed in accordance with a sequential contraceptive method without pause.

In the present methods the uninterrupted parenteral administration of the estrogenic component may usually occur at intervals of at least 12 hours, preferably of between 20 hours and 30 days. The relatively high in vivo halflife of the present estrogenic components in comparison to most known estrogens makes it feasible to employ administration intervals that are significantly longer than 1 day. With a view to compliance, however, it is preferred to employ once daily, once weekly or once monthly administration intervals. Naturally the length of the administration interval is largely determined by the mode of parenteral or rectal administration that is employed.

In accordance with the present invention the progestogenic component is advantageously administered in an amount which is effective to achieve a blood serum concentration which is equivalent to at least 50 pg/hl levonorgestrel, preferably of at least 200 pg/mL. In the present method, blood serum concentrations of the progestogenic component will usually remain below the equivalent of 10 ng/mL levonorgestrel. Preferably these concentrations remain below the equivalent of 2 ng/mL levonorgestrel.

In the present method the progestogenic component is usually administered in an amount of less than 1 mg per kg of bodyweight per day, preferably of less than 0.2 mg per kg of bodyweight per day. Furthermore, it is advisable to parenterally or rectally administer the progestogenic component in an amount of at least 0. 1 µg per kg of bodyweight per day. Preferably, the parenterally or rectally administered amount is at least 0.3 µg per kg of bodyweight per day.

In human females, the progestogenic component is usually parenterally or rectally administered in an average dosage of at least 5 µg per day, preferably of at least 15 µg per day. The maximum dosages normally remain below 50 mg per day, preferably below 10 mg per day.

Examples of progestogens which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterbne, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-nor-pregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestdne, dydrogesterone, precursors of these progestogens and mixtures thereof.

The present method also encompasses the co-administration of active principles in addition to the progestogenic and estrogenic component. For instance, androgens may advantageously be co-administered in order to prevent symptoms of hypoandrogenicity. Thus, a preferred embodiment of the invention comprises the co-administration of an androgenic component. The androgenic component is suitably co-administered in an effective amount to suppress symptoms of hypoandrogenicijy. Hypoandrogenicity in females has been associated with mood disturbances, unfavourable changes in haemostatic parameters and lack of bone mass.

The term "androgenic component" is defined as a substance that is capable of triggering an androgenic response in vivo or a precursor which is capable of liberating such a substance in vivo. Usually androgenic components are capable of binding to an androgen receptor.

Androgenic components that may suitably be employed in the present method may be selected from the group consisting of testosterone esters such as testosterone undecanoate, testosterone propionate, testosterone phenylpropionate, testosterone isohexanoate, testosterone enantate, testosterone bucanate, testosterone decanoate, testosterone buciclate; testosterone; danazol; gestrinone; methyltestosterone; dehydroepiandrosterone (DHEA); DHEA-sulphate; mesterolon; stanozolol; androstenedione; dihydrotestosterone; androstanediol; metenolon; fluoxymesterone; oxymesterone; methandrostenolol; MENT; precursors capable of liberating these androgens when used in the present method and mixtures thereof. Preferably the testosterone esters employed in the present method comprise an acyl group which comprises at least 6,more preferably from. 8-20 and preferably 9-13 carbon atoms. Androgens that can be used advantageously in the present method include testosterone esters,.testosterone and MENT. Most preferably the employed androgen is testosterone undecanoate.

In order to obtain the desired impact from the present method it is advisable to administer doses in an amount which leads to an increase in blood serum androgen level of at least 0.1 nmole testosterone equivalent per litre, preferably of at least 0.3 nmole testosterone equivalent per litre. Generally the method leads to an increase in blood serum androgen level of no more than 5 nmole testosterone equivalent per litre, preferably of less than 3 nmole testosterone equivalent per litre and most preferably of less than 1.5 nmole testosterone equivalent per litre.

The present method preferably does not employ a gonadotropin hormone releasing hormone composition as described in the aforementioned patents U.S. Pat. No. 5,211, 952,U.S. Pat. No. 5,340,584 and U.S. Pat. No. 5,340,585. Similarly, the present method preferably does not employ a luteinizing hormone releasing hormone composition as described in U.S. Pat. No. 4,762,717 and U.S. Pat. No. 5,130, 137. Furthermore, the present method preferably does not comprise the co-administration of an anti-progestogen as described in U.S. Pat. No. 5,468,736. The method may also suitably be applied without the co-administration of an antisense oligonucleotide that is complementary to the nucleotide sequence of the follicle stimulating hormone (FSH) receptor (WO 00/73416).

The present method is not suitable for oophorectomised females or for females in whom endometrial stimulation by estrogenic compositions is minimised or absent, e.g. as a result of hysterectomy.

Another aspect of the invention relates to a drug delivery system for parenteral or rectal administration that contain the estrogenic component as defined herein before and a progestogenic component as described herein before, which drug delivery system is selected from the group consisting of suppositories, systems for intravaginal delivery, injectable or implantable depot preparations, inhalers, nasal sprays and transdermal delivery systems, wherein the system contains at least 0.01 mg, preferably at least 0.05 mg of the estrogenic component. The system additionally contains a progestogenic component, preferably in an amount of at least 10 µg, more preferably it contains at least 30 µg of a progestogenic component.

In the present kit, the progestogenic component may conveniently be combined with the estrogenic component in a single parenteral or rectal dosage unit, e.g. a single transdermal patch, intravaginal ring, suppository or injection unit.

Transdermal delivery systems include patches, gels, tapes and creams, and can contain excipients such as solubilisers, permeation enhancers (e.g. fatty acids, fatty acid esters, fatty alcohols and amino acids), hydrophilic polymers (e.g. polycarbophil and polyvinyl pyrrolidine) and adhesives and tackifiers (e.g. polyisobutylenes, silicone-based adhesives, acrylates and polybutene).

Transmucosal delivery systems include patches, suppositories, pessaries, gels, and creams, and can contain excipients such as solubilizers and enhancers (e.g. propylene glycol, bile salts and amino acids), and other vehicles (e.g. polyethylene glycol, fatty acid esters and derivatives, and hydrophilic polymers such as hydroxypropylmethyl cellulose and hyaluronic acid).

Injectable depot systems include solutions, suspensions, gels, microspheres and polymeric injectables, and can comprise excipients such as solubility-altering agents (e.g. ethanol, propylene glycol and sucrose) and polymers (e.g. polycaprylactones, and PLGA's). Implantable depot systems include rods and discs, and can contain excipients such as PLGA and polycapryl lactone. Suitable fluid carrier components are physiologically compatible diluents wherein the active agents can be dissolved, suspended. An example of a diluent is water, with or without addition of electrolyte salts or thickeners. Thus, the depot formulation can be, for example, an aqueous microcrystalline suspension. Oils are particularly suitable as diluents, with or without the addition of a solubiliser, of a surfactant, or of a suspension or emulsifying agent. Examples of suitable oils include arachidis oil, olive oil, peanut oil, cottonseed oil, soybean oil, castor oil, and sesame oil. Examples of solubilisers include benzyl alcohol and benzyl benzoate. Depot preparations offer the advantage that a single injection or implantation suffices for one or several months. Duration of the depot effect depends the nature of the estrogenic component (the ester precursors being preferred as they display a slower release), the amount of the estrogenic component as well as on the type of carrier substance that releases the active agent. Generally, the duration will be in the range of 10-30 days, but longer or shorter times can also be achieved.

Other delivery systems that can be used for administering the pharmaceutical composition of the invention include intranasal and pulmonary delivery systems such as sprays and microparticles.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Vaginal cornification was chosen as a tissue-specific and estrogen-sensitive endpoint to determine the estrogenicity of estetrol (E4), after subcutaneous administration, in hypoestrogenic rats. 17β-estradiol (E2) and vehicle (10% ethanol/sesame oil) served as controls in the bioassay.

Uterine weight increase in the rat is more commonly used as a measure of estrogenicity. However, uterine weight also responds to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAAA, 81, 819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in appearance to a diestrous vaginal smear). Castrate vaginal smears are indicative that complete ovariectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given subcutaneously (sc) to ovariectomized adult rats. E2 was used as a positive control. The vehicle (10% ethanol/sesame oil) served as the negative control. Steroids were dissolved in absolute ethanol and then brought to the final concentration with sesame oil (10% ethanol in sesame oil). The occurrence of vaginal cornification, indicative of an estrogenic response, is an "all or none" response. Data are, therefore, expressed as the number of rats showing a vaginal estrogenic response over the number of rats (ratio) treated.

A vaginal estrogenic response occurred in 8/8 rats by day 2 and persisted through day in rats injected sc with 50 µg/kg/day E2 for 7 days (Table 1). Animals treated with the vehicle did not exhibit vaginal epithelial cornification (Table 1). The onset of vaginal epithelial cornification was dose-dependent in rats injected sc with 0.1, 0.3, 1.0, and 3.0 mg/kg/day E4 and started at the same day of treatment (Day 2) as observed for E2 (Table 1). At 0.1 mg/kg/day E4 already 4/8 rats and at 0.3 mg/kg/day E4 even 7/8 rats exhibited a vaginal estrogenic response by day 7. At 1.0 and 3.0 mg/kg/day E4 all rats showed a vaginal estrogenic response by day 7 (Table 1).

TABLE 1

Vaginal estrogenic response in ovariectomized rats treated subcutaneously (sc) with 17β-estradiol (E2) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day E2 | sc | 0/8 | 0/8 | 8/8 | 8/8 | 8/8 | 8/8 | 8/8 | 8/8 |
| Vehicle Control | sc | 0/8 | 0/8 | 0/8 | 0/8 | 0/8 | 0/8 | 0/8 | 0/8 |
| 0.1 mg/kg/day E4 | sc | 0/8 | 0/8 | 0/8 | 1/8 | 1/8 | 4/8 | 3/8 | 4/8 |
| 0.3 mg/kg/day E4 | sc | 0/8 | 0/8 | 1/8 | 5/8 | 7/8 | 6/8 | 7/8 | 7/8 |
| 1.0 mg/kg/day E4 | sc | 0/8 | 0/8 | 1/8 | 6/8 | 8/8 | 7/8 | 8/8 | 8/8 |
| 3.0 mg/kg/day E4 | sc | 0/8 | 0/8 | 3/8 | 8/8 | 8/8 | 8/8 | 8/8 | 8/8 |

Example 2

To determine the elimination half-life of estetrol (E4) after subcutaneous administration (sc), single dose studies were performed in female Sprague Dawley rats followed by frequent blood sampling over a 24 hours interval.

Female Sprague Dawley rats were equipped with a permanent silatic heart catheter, as described by Kuipers et al. (1985,Gastroenterology, 88, 403-411). Rats were allowed to recover from surgery for 5 days and were than administered 0.05, 0.5,or 5 mg/kg E4 in 0.5 ml arachidis oil. E4 was injected in the neck area using a 1 ml syringe and 20 g needle. Blood samples were subsequently collected via the heart catheter in heparinized tubes at 0.5, 1, 2, 4, 8 and 24 hours. Erythrocytes were removed by centrifugation at 5000×g for 10 minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient>0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, $AUC_{0-24}$ and half-life. Interestingly, E4 demonstrated a relatively long half-life of 2-3 hours, enabling the detection of bioactive levels of unconjugated E4 at all time points over a 24 hour interval.

Example 3

An established competitive steroid-binding assay (Hammond and Lahteenmaki. 1983. Clin Chem Acta 132: 101-110) was used to determine the relative binding affinity of estetrol (E4), 17α-ethiinylestradiol(EE2), 17β-estradiol (E2), testosterone (T)and 5α-dihydrotestosterone (DHT) for human sex Hormone Binding Globulin (SHBG).

Human SHBG was purified from transgenic mouse serum, as described previously (Avvakumov GV et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov GV et al., 2000. J Biol Chem 275: 25920-25925). The in vitro assay involved the use of the purified human SHBG and [$^3$H]DHT or [$^3$H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100 μl) of this human SHBG solution were then incubated with an equal volume of either [$^3$H]DHT or [$^3$H]estradiol at 10 nM, together with 100 μl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 μl) of an ice cold suspension of DCC were then added to each tube, and after a brief 2 seconds mixing, each tube was incubated in an ice bath for either 10 min or 5 min depending on whether [$^3$H]DHT or [$^3$H]estradiol were being used as labeled ligands, respectively. The unbound ligands adsorbed to DCC were then removed by centrifugation (2, 000×g for 15 min at 4 C), and the amounts of [$^3$H]labeled ligands bound to SHBG were counted in 2 ml ACS scintillation cocktail using in liquid scintillation spectrophotometer. The average amounts of [$^3$H]labeled ligands bound to SHBG at each concentration of competitor (B) were expressed as a percentage of the average amounts of [$^3$H] labeled ligands bound to SHBG in the absence of competitor ($B_0$), and were. plotted against the concentration of competitor in each assay tube. The results of the competitive binding assays are depicted in FIG. 1. As is clearly apparent from these competitive binding assays, estetrol does not bind at all to human SHBG when tested with either [$^3$H]DHT or [$^3$H] estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 4

A bioassay method is performed to investigate the antiovulatory activity of estetrol (E4), after subcutaneous (sc) administration, in four-day cyclic rats. 17α-ethinylestradiol (EE), 17β-estradiol (E2) and vehicle (10% ethanovsesame oil) serve as controls.

Rats are spontaneously ovulating, polyestrous mammals. Generally, proestrus lasts for 12 to 14 hours, estrus for 25 to 27 hours, metestrus for 6 to 8 hours, and diestrus for 55 to 57 hours (Freeman, 1988,In: The Physiology of Reproduction, E Knobil and J Neill (eds). Raven Press, Ltd, New York, pp. 1893-1928). These stages of the estrous cycle can be classified based on the cell types present in daily vaginal smears (Schwartz, 1969,Recent Prog. Horm. Res. 25, 1-55).

The preovulatory period of the rat estrous cycle is characterized by ovarian follicular growth and enhanced estrogen secretion. In the four-day cyclic rat, peripheral plasma levels of E2 are basal through estrus. At the end of metestnis and extending through early diestrus, plasma levels of E2 begin to rise. This increase continues through diestrus and early proestrus to reach peak values and plateau by mid-proestrus. Subsequently, E2 levels fall rapidly, reaching basal values by the early morning hours of estrus. The rising estrogen levels from late metestrus to early proestrus exert a positive feedback effect on the hypothalamic-pituitary axis resulting in a luteinizing hormone (LH) surge on the afternoon of proestrus. The LH surge induces follicular rupture and the release of ova in the early morning hours of estrus. By early afternoon on the day of estrus, ova are present in the ampulla of the oviduct and are readily visualized under a dissecting microscope.

Progesterone or levonorgestrel administered subcutaneously on diestrus to four-day is cyclic rats is known to inhibit ovulation and increased the estrous cycle length in a dose-dependent manner (Beattie and Corbin, 1975,Endocrinology 97, 885-890). It was shown that the progestational block of ovulation takes place predominately via the hypothalamic-pituitary axis. Retardation of follicular growth accompanies ovulatory inhibition at high doses of progestogen when both serum follicle stimulating hormone (FSH) and LH are significantly reduced (Beattie and Corbin, 1975,Endocrinology 97, 885-890). De Visser et al. (1984, (Arzneim. Forsch. 34, 1010-1020) have found that oral administration of EE to rats beginning on the day of estrus and-continuing through the estrous cycle blocked ovulation in a dose-dependent manner.

Vaginal smears from female rats are obtained daily for two weeks to select four-day cycling rats. Only four-day cyclic rats are to be used for the antiovulatory bioassay. Starting on the day of estrus, rats are sc dosed, twice daily at 6:30 am and 4:30 pm for 4 consecutive days, with vehicle control (10% ethanol/sesame oil), EE (1.0, 3.0, 30,or 100 µg/kg) E2 (0.1, 0.3, 1.0,or 3.0 mg/kg) or E4 (0.1 , 0.3, 1.0,or 3.0 mg/kg). One day after the final dose (day 5), rats are euthanized by $CO_2$ asphyxiation at 1 pm, and the number of ova per oviduct is determined. Group means are subsequently calculated for the number of ova per ovulated rat (both oviducts). The ratio of rats ovulating for each treatment group is compared to the ratio for the vehicle-treated rats.

The results obtained indicate that twice daily sc dosing of EE, E2 and E4 dose-dependently inhibits ovulation, whereas all rats receiving twice daily vehicle control ovulate. The results of E4 compare favorably to EE and E2. Similar to both EE and E2,complete ovulation inhibition is achieved with higher dosages of E4. Furthermore, E4's antiovulatory activity is of the same order of magnitude as E2,showing equal potency or even more potency in inhibiting ovulation than E2.

Example 5

Suitable formulations for the transdermal administration of estrogens are known in the art, and may be employed in the methods of the present invention. For example, suitable transdermal patch formulations for the administration of exogenous estrogen are described in U.S. Pat. No. 4,460,372 (Campbell et al.), U.S. Pat. No. 4,573,996 (Kwiatek et al.), U.S. Pat. No. 4,624,665 (Nuwayser), U.S. Pat. No. 4,722,941 (Eckert et al.), U.S. Pat. No. 5,223,261 (Nelson et al.), the disclosures of which are hereby incorporated by reference.

One suitable type of transdermal patch for use in the methods of the present invention includes a backing layer which is non-permeable, a permeable surface layer, an adhesive layer substantially continuously coating the permeable surface layer, and a reservoir located or sandwiched between the backing layer and the permeable surface layer such that the backing layer extends around the sides of the reservoir and is joined to the permeable surface layer at the edges of the permeable surface layer. The reservoir contains the estrogenic component and is in fluid contact with the permeable surface layer. The transdermal patch is adhered to the skin by the adhesive layer on the permeable surface layer, such that the permeable surface layer is in substantially continuous contact with the skin when the transdermal patch is adhered to the skin.

While the transdermal patch is adhered to the skin of the subject, the estrogenic component contained in the reservoir of the transdermal patch is transferred via the permeable surface layer, through the adhesive layer, and to and through the skin of the subject. The transdernal patch may suitably include one or more penetration-enhancing agents in the reservoir that enhance the penetration of the estrogenic component through the skin.

Examples of suitable materials which may comprise the backing layer are well known in the art of transdermal patch delivery, and any conventional backing layer material may be employed in the transdermal patch of the instant invention. Specific examples of suitable backing layer materials include but are not limited to polyester film, such as high density polyethylene, low density polyethylene or composites of polyethylene; polypropylene; polyvinyl chloride, polyvinylidene chloride; ethylene-vinyl acetate copolymers; and the like.

Examples of suitable permeable surface layer materials are also well known in the art of transdermal patch delivery, and any conventional material which is permeable to the estrogenic component, maybe employed in the transdermal patch of the instant invention. Specific examples of suitable materials for the permeable surface layer include but are not limited to dense or microporous polymer films such as those comprised of polycarbonates, polyvinyl chlorides, polyamides, modacrylic copolymers, polysulfones, halogenated polymers, polychloroethers, acetal polymers, acrylic resins, and the like. Specific examples of these types of conventional permeable membrane materials are described in U.S. Pat. No. 3,797,494 to Zaffaroni.

Examples of suitable adhesives which may be coated on the backing layer to provide the adhesive layer are also well known in the art and include, for example pressure sensitive adhesives such as those comprising acrylic and/or methacrylic polymers. Specific examples of suitable adhesives include polymers of esters of acrylic or methacrylic acid (e.g., n-butanol, n-pentanol, isopentanol, 2-methyl butanol, 1-methyl butanol, 1-methyl pentanol, 3-methyl pentanol, 3-methyl pentanol, 3-ethyl butanol, isooctanol, n-decanol, or n-dodecanol esters thereof) alone or copolymerized with ethylenically unsaturated monomers such as acrylic acid, methacrylic acid, acrylamnide, methacrylamide, N-alkoxymethyl acrylamides, N-alkoxymethyl methacrylamides, N-t-butylacrylamide, itaconic acid, vinyl acetate, N-branched C.sub. 10-24 alkyl maleamic acids, glycol diacrylate, or mixtures of the foregoing; natural or synthetic rubbers such as silicon rubber, styrene-butadiene rubber, butyl-ether rubber, neoprene rubber, nitrile rubber, polyisobutylene, polybutadiene, and polyisoprene; polyurethane elastomers; vinyl polymers such as polyvinyl alcohol, polyvinyl ethers, polyvinyl pyrrolidone, and polyvinyl acetate; ureaformraldehyde resins; phenol formaldehyde resins; resorcinol formaldehyde resins; cellulose derivatives such as ethyl cellulose, methyl cellulose, nitrocellulose, cellulose acetatebutyrate, and carboxymethyl cellulose; and natural gums such as guar, acacia, pectin, starch, destria, gelatin, casein, etc.

As will be apparent to those skilled in the art, the adhesive layer should be inert to the estrogenic component, and should not interfere with the transderrmal delivery of the estrogenic component through the permeable surface layer. Pressure sensitive adhesives are preferred for the adhesive layer of the transdermal patch to facilitate the application of the patch to the skin of the subject.

Suitable penetration-enhancing agents are well known in the art as well. Examples of conventional penetration-enhancing agents include alkanols such as ethanol, hexanol, cyclohexanol, and the like; hydrocarbons such as hexane, cyclohexane, isopropylbenzene; aldehydes and ketones such as cyclohexanone, acetamide; N,N-di(oower alkyl)acetamides such as N,N-diethylacetamide, N,N-dimethyl acetamide,; N-(2-hydroxyethyl)acetamide; esters such as N,N-diower alkyl sulfoxides; essential oils such as propylene glycol, glycerine, glycerol monolaurate, isopropyl myristate, and ethyl oleate; salicylates; and mixtures of any of the above.

In another example of a transdermal patch which is suitable for the transdermal delivery of the estrogenic component according to the present invention, said estrogenic component is incorporated into the adhesive layer rather than being contained in a reservoir. Examples of these types of patches are conventionally known and include, for example, the CLIMERA.®. patch available from Berlex. This type of transdermal patch comprises a backing layer and an adhesive/drug layer. The adhesive/drug layer has. the combined function of adhering the patch to the skin of the subject and containing the estrogenic component, which is to be administered. The active ingredient is leached from the adhesive/drug layer to and through the skin of the subject when the patch is adhered to the skin.

Any of the backing layers described herein above may be employed in this embodiment as well. In addition, any of the suitable adhesives described above may be employed. The adhesive/drug layer comprises a relatively homogeneous mixture of the selected adhesive and the active ingredient. Typically, the adhesive/drug layer comprises a coating substantially covering one surface of the backing layer. The adhesive/drug layer may also include a penetration enhancing agent such as those described above by incorporating the penetration enhancing agent into the substantially homogeneous mixture of the adhesive and the active ingredient.

As will be readily apparent to those skilled in the art, the transdermal patches according to the present invention may include a variety of additional excipients which are conventionally employed to facilitate the transdermal administration of the estrogenic component. Examples of such excipients include but are not limited to carriers, gelling agents, suspending agents, dispersing agents, preservatives, stabilisers, wetting agents, emulsifiing agents, and the like. Specific examples of each of these types of excipients are well known in the art and any conventional excipients may be employed in the transdermal patches of the instant invention.

The amount of estrogenic component contained in the transdermal patch formulations will depend upon the precise form of estrogenic component to be administered, but should be sufficient to deliver at least 20 μg per day. The amount of progestogenic component to be administered is typically equivalent to an amount of at least 20 μg levonorgestel per day. Typically, the transdermal patches are designed to be worn for several days before replacement is required. Thus the amount of estrogenic component in the patch must be sufficient to permit the administration of at least 20 μg per day for a period of several days. As an example, a transdermal patch according to the present invention which is designed to administer around 400 μg of estetrol and 20 μg levonorgestel per day for seven (7) days would contain approximately 40 mg of the estrogen and approximately 2 mg of the progestogen. Based upon this information, one skilled in the art would be able to establish the necessary amount of estrogenic component to be included in a given transdermal patch to achieve the delivery of the correct daily dose of estrogenic component.

Example 6

Suitable nontoxic pharmaceutically acceptable carriers for use in a drug delivery system for intranasal administration of the present estogenic component will be apparent to those skilled in the art of nasal pharmaceutical formulations. For those not skilled in the art, reference is made to "Remington's Pharmaceutical Sciences", 4th edition, 1970. Obviously, the choice of suitable carriers will depend on the exact nature of the particular nasal dosage form desired, e.g. whether the estrogenic component is to be formulated into a nasal solution (for use as drops or as a spray), nasal microspheres, a nasal suspension, a nasal ointment or a nasal gel, as well as on the identity of the estrogenic component.

Examples of the preparation of typical nasal compositions are set forth below.

Nasal Solution:
  15 mg of estetrol and 15 mg of progesterone are combined with 10 mg of Tween 80. That mixture is then combined with a quantity of isotonic saline sufficient to bring the total volume to 50 ml. The solution is sterilised by being passed through a 0.2 micron Millipore filter.

Nasal Gel:
  250 ml of isotonic saline are heated to 80° C. and 1.5 g of Methocel are added, with stirring. The resultant mixture is allowed to stand at room temperature for 2 hours. Then, 25 mg of estetrol and 25 mg of progesterone are mixed together with 10 mg of Tween 80. The estetrdl/Tween mixture and a quantity of isotonic saline sufficient to bring the total volume to 500 ml were added to the gel and thoroughly mixed.

Example 7

The intravaginal drug delivery vehicle may suitably take the form of a vaginal ring. Vaginal rings are torous shaped devices designed to deliver a relatively constant dose of drug to the vagina usually over a period of weeks to months. Typically, they are made of a poly. EVA elastomer and the estrogenic component is released by diffusion though the elastomer. The vaginal ring is designed to regulate the release rate of the estrogenic component so as to provide the user with the appropriate daily dose. Among the important factors governing release are the solubility of the estrogenic component in the ring elastomer, the surface area of the drug reservoir, the distance the drug must diffuse through the ring body to reach its surface and the molecular weight of the drug.

If relatively high release rates are desired, they can be attained by a drug load at the ring surface as is characteristic of the homogeneous matrix ring design. This design, however, suffers from rapidly declining release rates as the distance the drug must travel to reach the ring surface increases as the drug load near the surface is depleted. If moderately high release rates are needed to provide the appropriate dose, a design which modulates release rate by imposing a layer of drug-free elastomer between the drug reservoir and the ring exterior is appropriate. This may be attained by coating a homogeneous ring, or to conserve drug, by incorporating a drug-free core, a shell design may be used. If an even lower release rate is desired, the drug may be confined to a small diameter at the center of the ring ("core ring"). Numerous types of vaginal rings have been described in the patent and non-patent literature alike.

An example of the preparation of an estetrol containing intravaginal ring is set forth below:

Four 58 nmm core rings are prepared as follows. Fifty grams of Silastic 382® are mixed with 0.3 g of stannous octoate, transferred to a 50 cc plastic syringe and injected into four brass ring moulds. After 45 minutes, the moulds are opened, the rings removed, the flash is trimmed and the rings are cut open at a 45° angle. A mixture of 84.4 g Silastic 382®, 24.2 g of micronised estetrol and 12.2 g micronised levonorgestrel are mixed in a Teflon bowl. The mixture is transferred to a Lucite coating cup with a bottom opening of 8.7 mm. The open rings are heated at 110° C. for 30 minutes, cooled and weighed. The open rings weigh approximately 9.8 g. The open rings are pulled through the coating cup and dipped in a solution of 0.67% stannous octoate in toluene (w/v). The open ring is again heated at 110° C. for 30 minutes and reweighed. The weight of the coated open ring is approximately 10.3 g and the weight of the coating on the open rings is therefore approximately 0.5 g.

In order to apply the outer layer a 16.5 cm long piece of silicone rubber tubing having 6.3 mm diameter and 0.3 mm wall thickness is swollen in hexane and the open ring coated with the medicated layer is placed inside the silicone rubber tubing. The hexane is evaporated at room temperature and the tubing contracted to the size of the open ring forming an outer layer having a thickness of 0.2 mm.

The excess tubing is trimmed flush with the ends of the open ring and Dow Corning Medical Adhesive A is applied at both ends of the open ring and to 1 cm of the outer layer at both ends of the open ring. A 4 cm piece of silicone tubing 6.3 mm inner diameter and 0.3 mm wall thickness is swollen with hexane and placed over the two ends of the open ring to close the ring. The ring is held for about two minutes until the tubing has shrunk and fits snugly over the ring junction. The adhesive is allowed to cure for 24 hours, the rings are rinsed in alcohol and air dried.

Example 8

An estetrol containing depot formulation can suitably be prepared as set forth below.

At room temperature, 1000 mg estetrol and 1500 mg levonorgestrel are dispersed in 6 millilitre dehydrated ethanol. This solution is then diluted with 660 ml arachidis oil under thorough stirring. The resulting solution is sterilised by filtration.

In case an estetrol ester is used, e.g. estetrol valerate esters, a significantly lower release rate can be obtained. Such low release rates are particularly advantage if the depot injections are to be administered at relatively long time intervals, e.g. intervals of more than 1 week.

The invention claimed is:

1. A drug delivery system for parenteral, or rectal administration, comprising an estrogenic component and a progestogenic component, said drug delivery system being selected from the group consisting of suppositories, systems for intravaginal delivery, injectable or implantable depot preparations, inhalers, nasal sprays and transdermal delivery systems, wherein the system contains at least 0.01 mg of the estrogenic component, wherein said estrogenic component is selected from the group consisting of substances represented by the following formula:

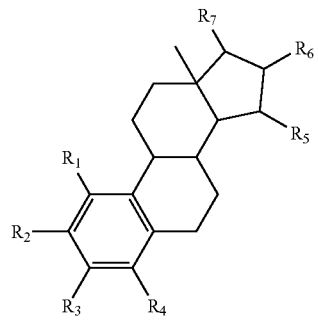

in which formula $R_1$, $R_2$, $R_3$, $R_4$, independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;

precursors capable of liberating a substance according to the aforementioned formula when used in the present method, which precursors are derivatives of the substances represented by the formula, wherein the hydrogen atom of at least one of the hydroxyl groups in said formula has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of one or more of the aforementioned substances and/or precursors, and wherein the system does not contain a luteinizing hormone releasing hormone (LHRH) composition or a gonadotropin hormone releasing hormone (GnRH) composition.

2. The drug delivery system according to claim 1, wherein the device contains at least 10 µg of the progestogenic component.

* * * * *